United States Patent
Wu et al.

(10) Patent No.: US 9,622,674 B2
(45) Date of Patent: Apr. 18, 2017

(54) METHOD AND SYSTEM FOR GENERATING TWELVE-LEAD ELECTROCARDIOGRAM SIGNALS USING THREE DIFFERENTIAL VOLTAGES

(71) Applicant: National Chiao Tung University, Hsinchu (TW)

(72) Inventors: Sau-Hsuan Wu, New Taipei (TW); Chih-Hao Hsu, Taichung (TW)

(73) Assignee: National Chiao Tung University, Hsinchu (TW)

(*) Notice: Subject to any disclaimer, the term of this patent is extended or adjusted under 35 U.S.C. 154(b) by 0 days.

(21) Appl. No.: 14/735,731

(22) Filed: Jun. 10, 2015

(65) Prior Publication Data
US 2016/0157744 A1    Jun. 9, 2016

(30) Foreign Application Priority Data
Dec. 9, 2014    (TW) .............. 103142878 A

(51) Int. Cl.
*A61B 5/0402* (2006.01)
*A61B 5/0408* (2006.01)
*A61B 5/00* (2006.01)

(52) U.S. Cl.
CPC .......... *A61B 5/04028* (2013.01); *A61B 5/72* (2013.01); *A61B 5/0006* (2013.01); *A61B 5/04085* (2013.01); *A61B 5/6823* (2013.01)

(58) Field of Classification Search
None
See application file for complete search history.

(56) References Cited

U.S. PATENT DOCUMENTS

| 4,318,412 A | * | 3/1982 | Stanly | A61B 5/0006 600/508 |
| 4,850,370 A | * | 7/1989 | Dower | A61B 5/04011 600/512 |
| 5,168,874 A | * | 12/1992 | Segalowitz | A61B 5/0006 128/903 |
| 5,339,823 A | * | 8/1994 | Reinhold, Jr. | A61B 5/0006 128/904 |
| 6,633,857 B1 | | 10/2003 | Tipping | |

(Continued)

OTHER PUBLICATIONS

Chih-Hao Hsu & Sau-Hsuan Wu, "Robust Signal Synthesis of the 12-Lead ECG using 3-Lead Wireless ECG Systems," IEEE ICC Jun. 11, 2014.

(Continued)

*Primary Examiner* — Kennedy Schaetzle
(74) *Attorney, Agent, or Firm* — Cesari and McKenna, LLP; James A. Blanchette

(57) ABSTRACT

In a method and system for generating twelve-lead ECG signals based on three differential voltages, each of which is defined as a potential difference between two myoelectric signals sensed respectively by two corresponding electrodes that cooperatively constitute a corresponding differential electrode pair and that are disposed on a user's chest at predetermined specific locations, a signal processor generates the twelve-lead ECG signals using a pre-established dynamic system model that is associated with the specific locations of the electrodes on the user's chest and that is configured with temporal and spatial correlations among twelve leads of an ECG.

19 Claims, 6 Drawing Sheets

(56) References Cited

U.S. PATENT DOCUMENTS

| | | | |
|---|---|---|---|
| 6,636,761 B2 | 10/2003 | Brodnick | |
| 6,721,591 B2 | 4/2004 | Wei et al. | |
| 6,813,514 B1* | 11/2004 | Kroll | A61B 5/0452 |
| | | | 600/509 |
| 6,829,501 B2* | 12/2004 | Nielsen | A61B 5/02055 |
| | | | 600/513 |
| 6,901,285 B2 | 5/2005 | Schreck | |
| 7,184,819 B2* | 2/2007 | Tabbara | A61B 5/7475 |
| | | | 600/523 |
| 8,315,695 B2 | 11/2012 | Sebelius | |
| 9,351,654 B2* | 5/2016 | Albert | A61B 5/6898 |
| 2003/0023175 A1* | 1/2003 | Arzbaecher | A61B 5/0006 |
| | | | 600/509 |
| 2006/0009691 A1* | 1/2006 | Yeo | A61B 5/0245 |
| | | | 600/386 |
| 2006/0224071 A1* | 10/2006 | Stewart | A61B 5/0006 |
| | | | 600/509 |
| 2010/0234746 A1* | 9/2010 | Sebelius | A61B 5/0006 |
| | | | 600/509 |
| 2016/0073914 A1* | 3/2016 | Lapetina | A61B 5/681 |
| | | | 600/384 |

OTHER PUBLICATIONS

Roman Trobec & Ivan Tomasic, "Synthesis of the 12-Lead Electrocardiogram from Differential Leads," IEEE Transactions on Information Technology in Biomedicine, vol. 15, No. 4, Jul. 2011.

\* cited by examiner

METHOD AND SYSTEM FOR GENERATING TWELVE-LEAD ELECTROCARDIOGRAM SIGNALS USING THREE DIFFERENTIAL VOLTAGES

CROSS-REFERENCE TO RELATED APPLICATION

This application claims priority to Taiwanese Application No. 103142878, filed on Dec. 9, 2014, the contents of which are hereby incorporated by reference.

FIELD

The disclosure relates to generation of twelve-lead electrocardiogram (ECG), and more particularly to a method and system for generating twelve-lead ECG signals using three differential leads.

BACKGROUND

A twelve-lead electrocardiogram has become a widely used non-invasive standard in diagnosing heart diseases, such as ischemic heart disease and acute myocardial infarction.

FIG. 1 illustrates a conventional twelve-lead electrocardiogram system for a human body. In the conventional twelve-lead electrocardiogram system, ten electrodes (RL, LL, RA, LA, $V_1$-$V_6$) are attached to the surface of the human body, wherein the electrodes ($V_1$-$V_6$) are positioned on the chest of the human body, and the electrodes (RL, LL, RA, LA) are positioned on the limbs of the human body. The electrode (RL) is used as a reference ground, and heart potentials (vF, vR, vL, v1-v6) sensed respectively by the electrodes (LL, RA, RL, $V_1$-$V_6$) are input to an apparatus 200, namely an electrocardiograph. The apparatus 200 produces twelve-lead electrocardiogram that includes six waveforms of limb leads, named as I, II, III, aVR, aVL and aVF, and six waveforms of chest leads, named as V1, V2, V3, V4, V5 and V6, with the following definitions.

TABLE 1

| Lead | Definition |
|---|---|
| I | vL − vR |
| II | vF − vR |
| III | vF − vL |
| aVR | vR − (vL + vF)/2 |
| aVL | vL − (vR + vF)/2 |
| aVF | vF − (vL + vR)/2 |
| V1 | v1 − (vR + vL + vF)/3 |
| V2 | v2 − (vR + vL + vF)/3 |
| V3 | v3 − (vR + vL + vF)/3 |
| V4 | v4 − (vR + vL + vF)/3 |
| V5 | v5 − (vR + vL + vF)/3 |
| V6 | v6 − (vR + vL + vF)/3 |

The leads (I, II, V1-V6) are regarded as independent leads, and the leads (III, aVR, aVL, aVF) are regarded as non-independent leads.

However, mounting and maintaining attachment of such ten electrodes (RL, LL, RA, LA, $V_1$-$V_6$) to record the twelve-lead electrocardiogram are almost impractical. For a patient, it is very difficult to do this for long-term bedside monitoring because the number of the electrodes (RL, LL, RA, LA, $V_1$-$V_6$) and the conventional configuration severely restrict the mobility of the patient.

SUMMARY

Therefore, an object of the disclosure is to provide a method and system for generating twelve-lead electrocardiogram (ECG) signals using three differential electrode pairs that are suitable for long-term ECG measurement and monitoring of a user's body with relatively high accuracy and without restriction to mobility of the user.

According to one aspect of the disclosure, there is provided a method of generating twelve-lead electrocardiogram (ECG) signals to be implemented by a signal processor. The method of this disclosure includes the steps of:

a) receiving three differential voltages, each of which is defined as a potential difference between two corresponding myoelectric signals sensed respectively by two corresponding electrodes that constitute a corresponding differential electrode pair and that are disposed on a chest of a user's body at predetermined specific locations; and b) generating, based on the differential voltages, the twelve-lead ECG signals, which include twelve synthesized lead signals, using a pre-established dynamic system model that is associated with the specific locations of the electrodes constituting the differential electrode pair on the chest of the user's body and that is configured with temporal and spatial correlations among the signals of the twelve leads of an ECG, which include eight independent leads and four non-independent leads.

According to another aspect of the disclosure, there is provided a system for generating twelve-lead electrocardiogram (ECG) signals. The system of this disclosure includes:

three signal sensing devices attachable to a chest of a user's body, each of the signal sensing devices including two spaced apart electrodes that cooperatively constitute a corresponding differential electrode pair and that are to be disposed on the chest of the user's body at predetermined specific locations, and being configured to sense two myoelectric signals of the user's body through the electrodes thereof so as to generate a corresponding distinct differential voltage that is defined as a potential difference between the myoelectric signals; and a signal processing terminal for receiving the differential voltages respectively therefrom in a wireless manner, the signal processing terminal being operable to generate, based on the differential voltages, the twelve-lead ECG signals, which include twelve synthesized lead signals, using a pre-established dynamic system model that is associated with the specific locations of the electrodes constituting the differential electrode pair of the signal sensing devices on the chest of the user's body and that is configured with temporal and spatial correlations among the signals of the twelve leads of an ECG, which include eight independent leads and four non-independent leads.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
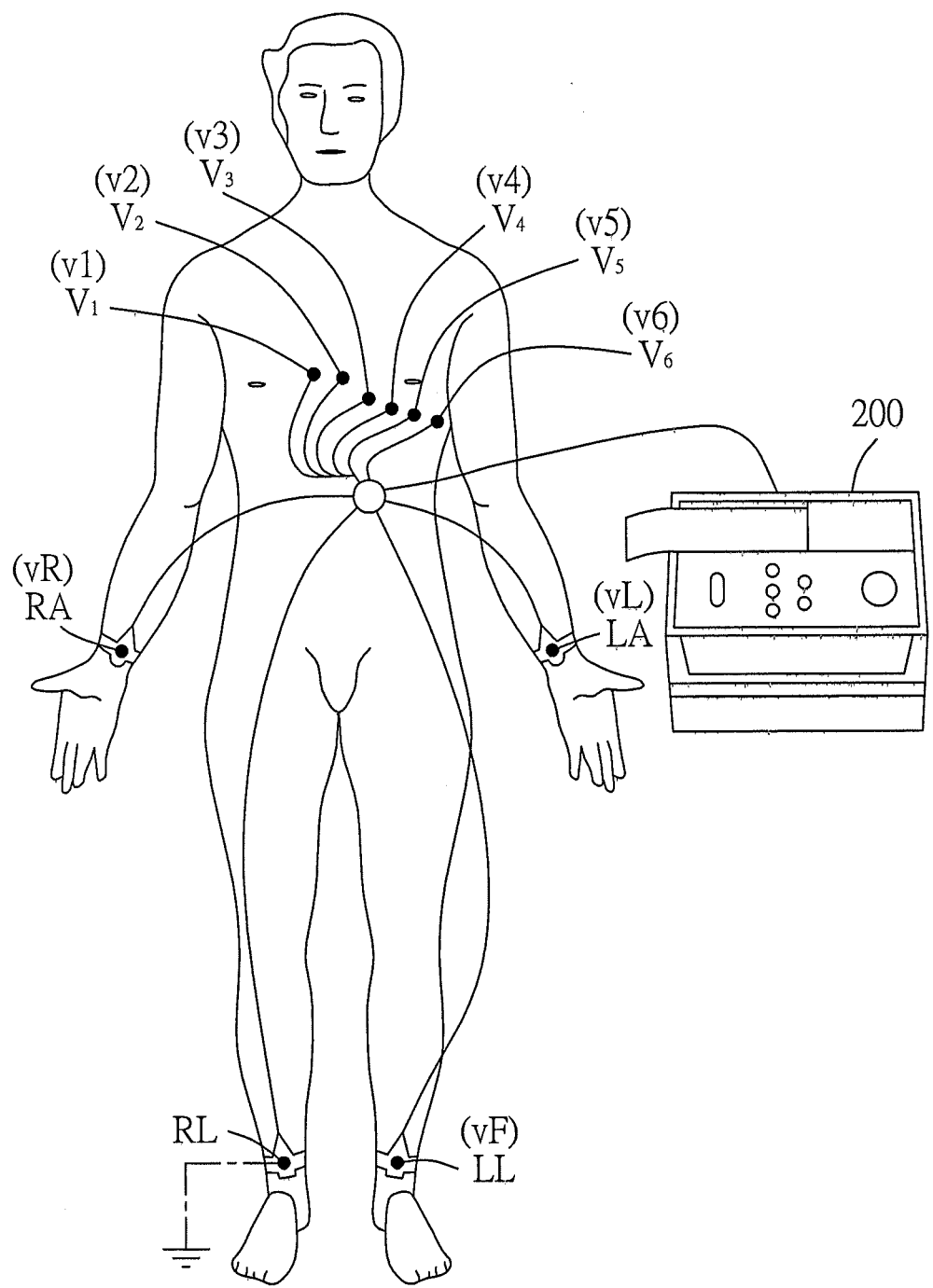
FIG. 1 is a schematic view illustrating mounting and configuration of a conventional twelve-lead electrocardiogram system for a human body.

Before the disclosure is described in greater detail, it should be noted herein that like elements are denoted by the same reference numerals throughout the disclosure.

Figure 2:
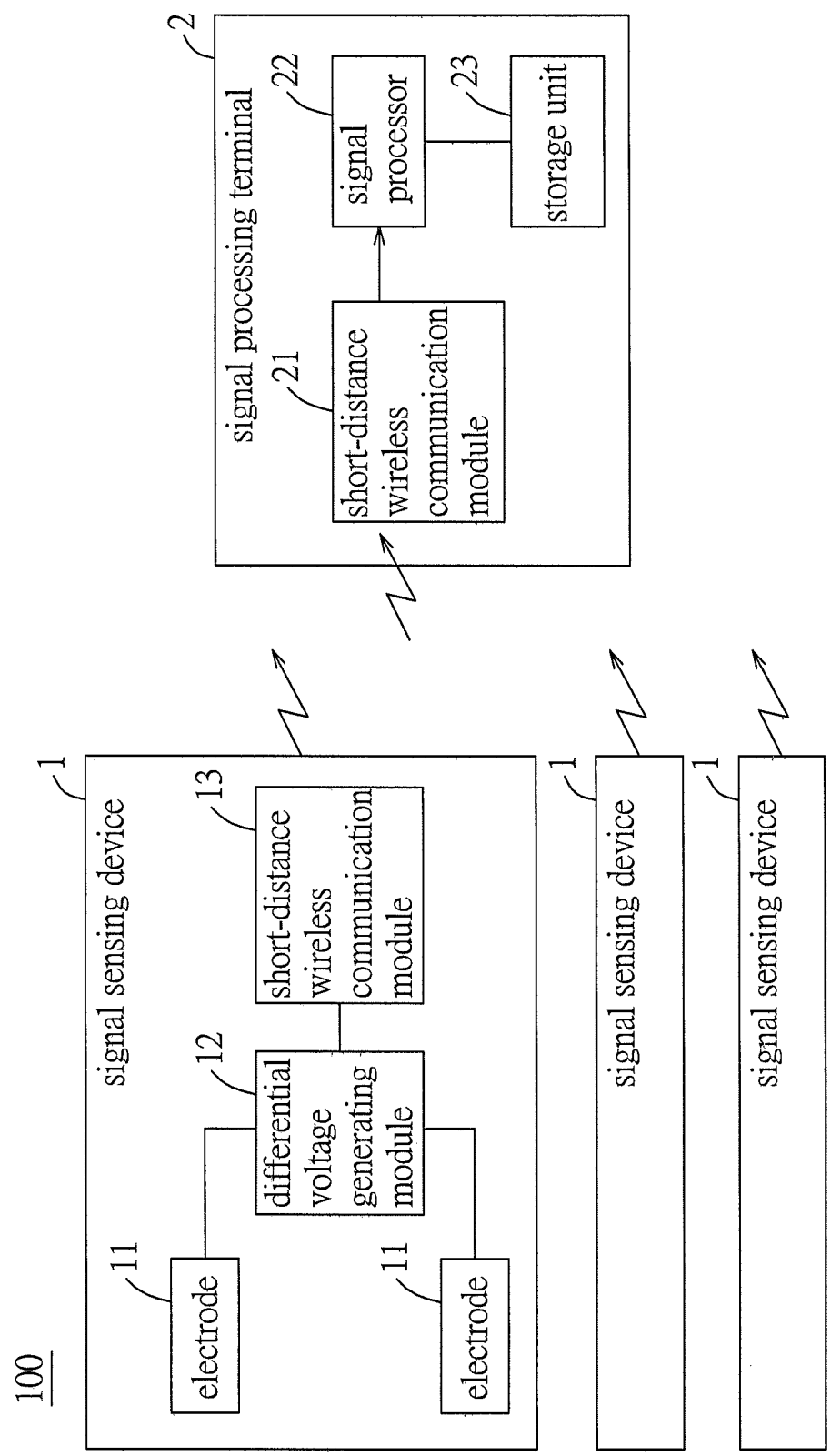
FIG. 2 is a schematic block diagram illustrating the first embodiment of a system for generating twelve-lead electrocardiogram (ECG) signals according to the disclosure.
Figure 3:
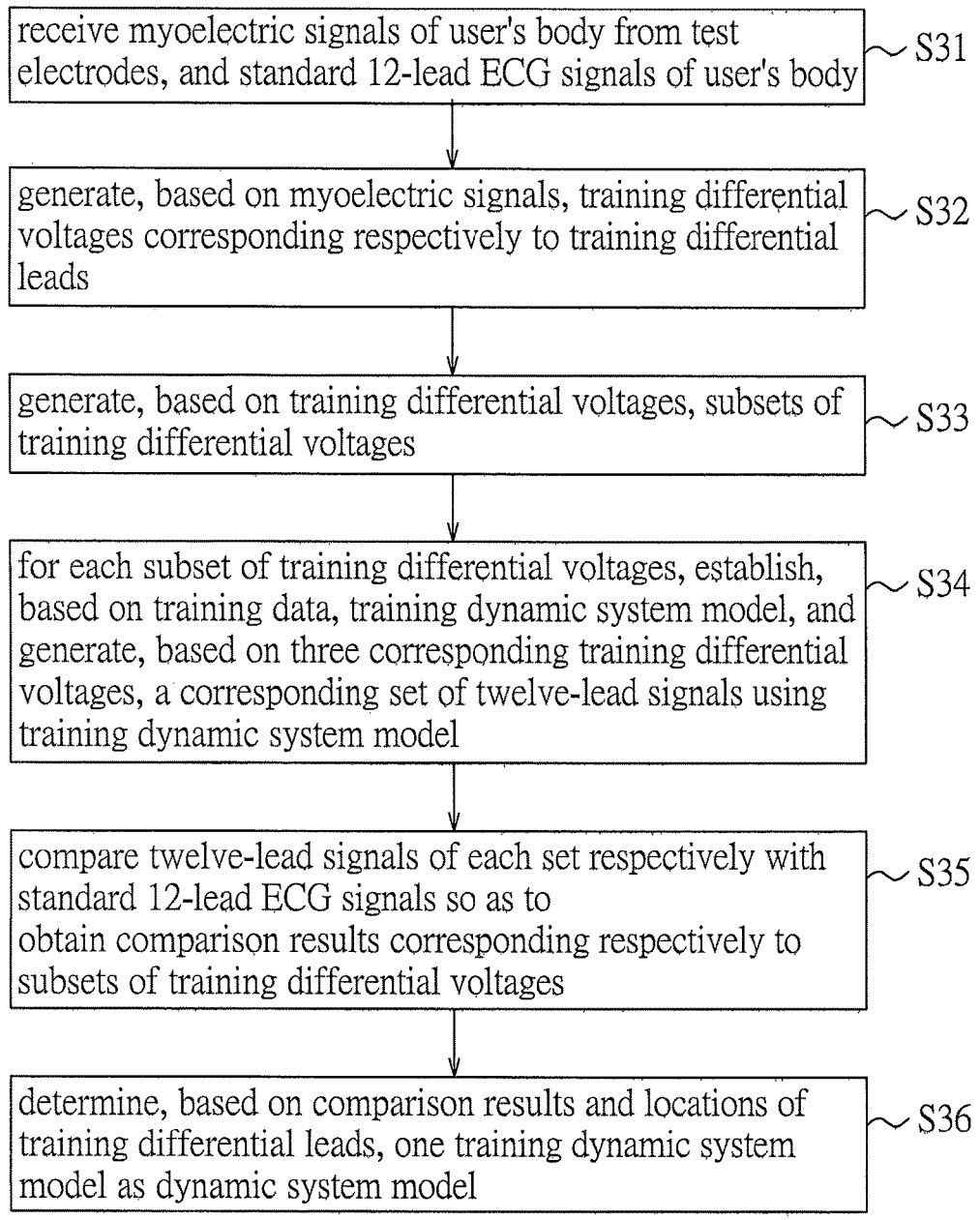
FIG. 3 illustrates a training procedure of how to establish a dynamic system model used in the first embodiment.

Referring to FIG. 2, the first embodiment of a system 100 for generating twelve-lead electrocardiogram (ECG) signals (interchangeably referred to as synthesized twelve-lead ECG signals herein) according to this disclosure is shown to include three signal sensing devices 1 and a signal processing terminal 2. The synthesized twelve-lead ECG signals may be subsequently used to form an ECG to be displayed on a monitor for view by, e.g., a medical staff.

The signal sensing devices 1 are attachable to a chest of a user's body (not shown). In this embodiment, each signal sensing device 1 exemplarily includes two spaced apart electrodes 11, a differential voltage generating module 12, and a short-distance wireless communication module 13.

For each signal sensing device 1, the electrodes 11 are placed at predetermined specific locations on the chest of the user's body and arranged in a manner that a distance therebetween ranges, for example, from 10 cm to 15 cm, and cooperatively constitute a corresponding differential electrode pair to sense two myoelectric signals, of the user's body. For example, the locations of the electrodes 11 of the differential electrode pairs of the signal sensing devices 1 are around a heart of the user's body. The differential voltage generating module 12 is connected electrically to the electrodes 11, and receives the myoelectric signals from the electrodes 11 so as to generate a corresponding differential voltage that is defined as a potential difference between the myoelectric signals. The short-distance wireless communication module 13, such as a ZigBee module, is connected to the differential voltage generating module 12, and is operable to transmit the differential voltage from the differential voltage generating module 12 via short-distance wireless communication.

In this embodiment, the signal processing terminal 2 exemplarily includes a short-distance wireless communication module 21 that communicates with the short-distance wireless communication modules 13 of the signal sensing devices 1 in a short-distance wireless manner, a signal processor 22 that is coupled to the short-distance wireless communication module 21, and a storage unit 23 that is coupled to the signal processor 22. It is noted that the signal processing terminal 2 may be implemented as a mobile device, for example, a smart phone, a tablet computer or the like, carried on the user.

Figure 4:
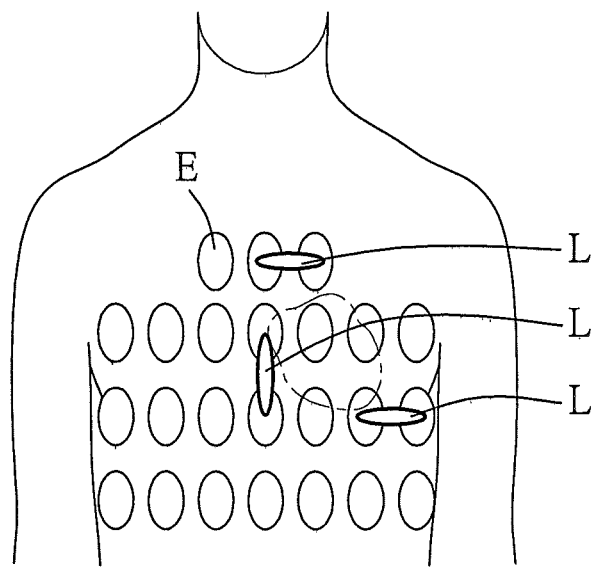
FIG. 4 is a schematic view exemplarily illustrating an arrangement of electrodes of three differential electrode pairs of the first embodiment on a chest of a user's body.

Prior to operation of the system 100 on the user, initially, the signal processor 22 of the signal processing terminal 2 cooperates with a plurality of additional test electrodes, for example, twenty-four test electrodes (E) shown in FIG. 4, to perform a training procedure on establishing a dynamic system model, which is associated with the patient and which is to be used in the system 100 of the first embodiment when generating the synthesized twelve-lead ECG signals for the user. In this embodiment, referring to FIG. 4, the test electrodes (E) are applied to the chest of the user's body at separate points. More specifically, the test electrodes (E) may be two-dimensionally arranged in a manner that a distance between any two adjacent test electrodes (E) ranges, for example, from 10 cm to 15 cm. After completion of the training procedure, the placement locations of the electrodes 11 that constitute the differential electrode pairs of the signal sensing devices 1 on the chest of the user's body can be determined. The training procedure includes the following steps.

In step S31, the signal processor 22 receives a plurality of training myoelectric signals, which are sensed respectively by the test electrodes (E) during a training period of, for example, 10 seconds, and twelve standard lead signals measured from the user's body during the training period. It should be appreciated that the twelve standard lead signals cooperatively constitute a standard twelve-lead ECG.

In step S32, the signal processor 22 generates, based on the training myoelectric signals, a plurality of training differential voltages that correspond respectively to a plurality of training differential electrode pairs, each of which consists of a respective adjacent pair of the test electrodes (E) that are disposed at respective distinct locations on the chest of the user's body. Each of the training differential voltages is defined as a potential difference between two of the training myoelectric signals sensed by two corresponding adjacent ones of the test electrodes (E).

In step S33, the signal processor 22 generates, based on the training differential voltages, a plurality of different training differential voltage subsets, each containing three corresponding ones of the training differential voltages.

In step S34, for each of the training differential voltage subsets, the signal processor 22 establishes, based on the three training differential voltages and on the twelve standard lead signals, a training dynamic system model that is associated with three of the training differential electrode pairs which correspond respectively to the three training differential signals and that is configured with temporal and spatial correlations among the twelve leads of a typical (i.e., conventionally defined) twelve-lead ECG, which include eight independent leads and four non-independent leads, and generates, based on the three corresponding ones of the training differential voltages and on the training dynamic system model, a corresponding set of twelve synthesized lead signals, which include eight independent synthesized lead signals corresponding respectively to the eight independent leads of the typical twelve-lead ECG, and four non-independent synthesized lead signals corresponding respectively to the four non-independent leads of the typical twelve-lead ECG. It is noted that, for each of the training differential voltage subsets, the three corresponding training differential voltages generated based on those training myoelectric signals that are measured within a portion of the training period, for example, the first three seconds of the period of ten seconds and the twelve standard lead signals measured within the same portion of the training period constitute training data that is used to establish the training dynamic system model, and the three corresponding training differential voltages generated based on those training myoelectric signals that are measured within the rest of the training period are used to generate the corresponding set of the twelve synthesized lead signals.

In this embodiment, for each of the training differential voltage subsets, the training dynamic system model can be defined by the following expressions (1), (2) and (3):

$$x[n]=\tilde{H}\tilde{s}[n]+w[n] \quad (1)$$

$$\tilde{s}[n]=[s[n]^T, s[n-1]^T, \ldots, s[n-L+1]^T]^T \quad (2)$$

$$\tilde{H}=[H_{3\times 8} 0_{3\times 8(L-1)}] \quad (3)$$

where x[n] is a 3×1 vector and represents the three corresponding ones of the training differential voltages at time n, š[n] is an 8L×1 vector and represents signals at time n that correspond respectively to the eight independent leads (i.e., the leads (I, II, V1-V6)) of the twelve leads, that characterize the temporal and spatial correlations among the eight independent leads and that conform to an $L^{th}$-order autoregression (AR(L)) model, L is a predetermined order number that equals, for example, 3, H̃ is a 3×8L matrix and is associated with a transformation matrix $H_{3\times 8}$ obtained from the training data, and w[n] is a 3×1 noise vector at time n and is obtained from the training data.

Using the AR(L) model, š[n] can be further dynamically represented by the following expression (4)

$$\tilde{s}[n]=F\tilde{s}[n-1]+Bv[n] \quad (4)$$

where F is an 8L×8L matrix and characterizes the temporal and spatial correlations among the eight independent leads of the twelve leads, B is an 8L×8 noise power matrix, and v[n] is an 8×1 noise vector at time n. In this embodiment, using Wiener-Hopf equation, F can be obtained based on the training data. In this case, for each of the individual training differential voltage subsets, the corresponding set of the twelve synthesized lead signals can be generated based on x[n], š[n] and H̃ using filtering processing.

When expressions (3) and (4) are introduced into expression (1) while the noise is filtered out through filtering operation by, for example, a Kalman filter, for each of the individual training differential voltage subsets, the eight independent lead signals ŝ[n] of the corresponding set of twelve synthesized lead signals can be represented by the following expression $$\hat{s}[n]=F\hat{s}[n-1]+K[n](x[n]-\tilde{H}F\hat{s}[n-1])$$

where K[n] is an 8L×3 filter gain matrix at time n. Thus, the four non-independent lead signals of the corresponding set of twelve synthesized lead signals can be generated based on ŝ[n].

In step S35, the signal processor 22 compares the corresponding set of twelve synthesized lead signals of each of the training differential voltage subsets respectively with the twelve standard lead signals within the rest (i.e., the later seven seconds) of the period of ten seconds, so as to obtain comparison results corresponding respectively to the different training differential voltage subsets. In this embodiment, for each of training differential voltage subsets, twelve correlation coefficients (CCs) each between a corresponding one of the synthesized lead signals of the corresponding set of the twelve synthesized lead signals and a corresponding one of the twelve standard lead signals measured within the rest of the period of ten seconds, and/or, for example, a smallest one ($CC_{min}$) of the correlation coefficients (CCs) cooperatively serve as a corresponding comparison result.

In step S36, the signal processor 22 selects, based on the comparison results of all the training differential signal subsets, one of the training dynamic system models established in step S34 as the dynamic system model for the user, and takes the locations of the test electrodes (E) constituting the three corresponding ones of the training differential electrode pairs associated with said one of the training dynamic system models to be the specific locations of the electrodes 11 of the differential electrode pairs of the signal sensing devices 1. It is noted that the three training differential signals of the training differential voltage subsets associated with said one of the training dynamic system models may be regarded as three target differential voltages. The three corresponding ones of the training differential electrode pairs associated with said one of the training dynamic system models, i.e., those corresponding respectively to the three target differential voltages, may be regarded as three target differential electrode pairs. The twelve correlation coefficients (CCs) associated with the three target differential voltages are relatively large, i.e., generally greater than 0.95.

Figure 5:
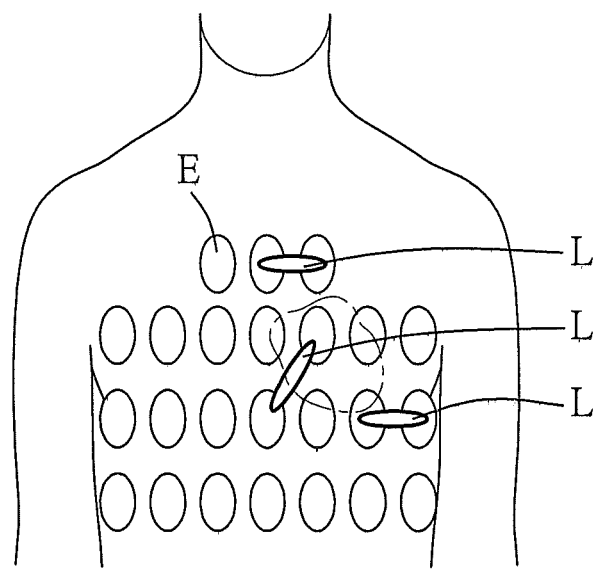
FIG. 5 is a schematic view exemplarily illustrating another arrangement of the electrodes of the three differential electrode pairs of the first embodiment on the chest of the user's body.

According to experimental results, the three target differential electrode pairs may be arranged as shown in FIG. 4 or 5, with each element indicated by the label (L) representing a corresponding signal sensing device 1 including a corresponding differential electrode pair.

That is to say, the placement locations of the electrodes 11 that constitute the differential electrode pairs of the signal sensing devices 1 correspond to the center locations on the user's chest to which the six test electrodes (E) that are overlapped by the elements (L) in FIGS. 4 and 5 are placed and the placement orientations of the signal sensing devices 1 are as shown by the elements (L). In other words, the specific locations of the electrodes 11 of the signal sensing devices 1 may be at a position between the upper right side edge of the heart of the user's body and a collarbone of the user's body, on the lower left side edge of the heart of the user's body, and on the right side of the heart of the user's body, respectively. It should be noted that, since a human body is generally less susceptible to fat accumulation at these locations, noise interference caused by fat can be reduced. In addition, the signal sensing devices 1 can be sized similarly to a medium adhesive tape. Therefore, the signal sensing devices 1 are suitable for all users having different body types. Furthermore, from the experimental results, since all the correlation coefficients (CCs) associated with the target differential voltages are generally greater than 0.95, the dynamic system model used in the first embodiment can ensure the accuracy of the twelve synthesized lead signals generated, i.e., the substantially close resemblance between the synthesized twelve-lead ECG signals including the twelve synthesized lead signals and typical twelve-lead ECG signals acquired using ten electrodes in the conventional way.

Referring again to FIG. 2, upon receipt of the differential voltages respectively from the signal sensing devices 1 through short-distance wireless communication, the short-distance wireless communication module 21 transmits the differential voltages to the signal processor 22. Thus, the signal processor 22 generates, based on the differential voltages, the synthesized twelve-lead ECG signals using the dynamic system model in the above manner. The synthesized twelve-lead ECO signals associated with the user's body are then stored in the storage unit 23.

Figure 6:
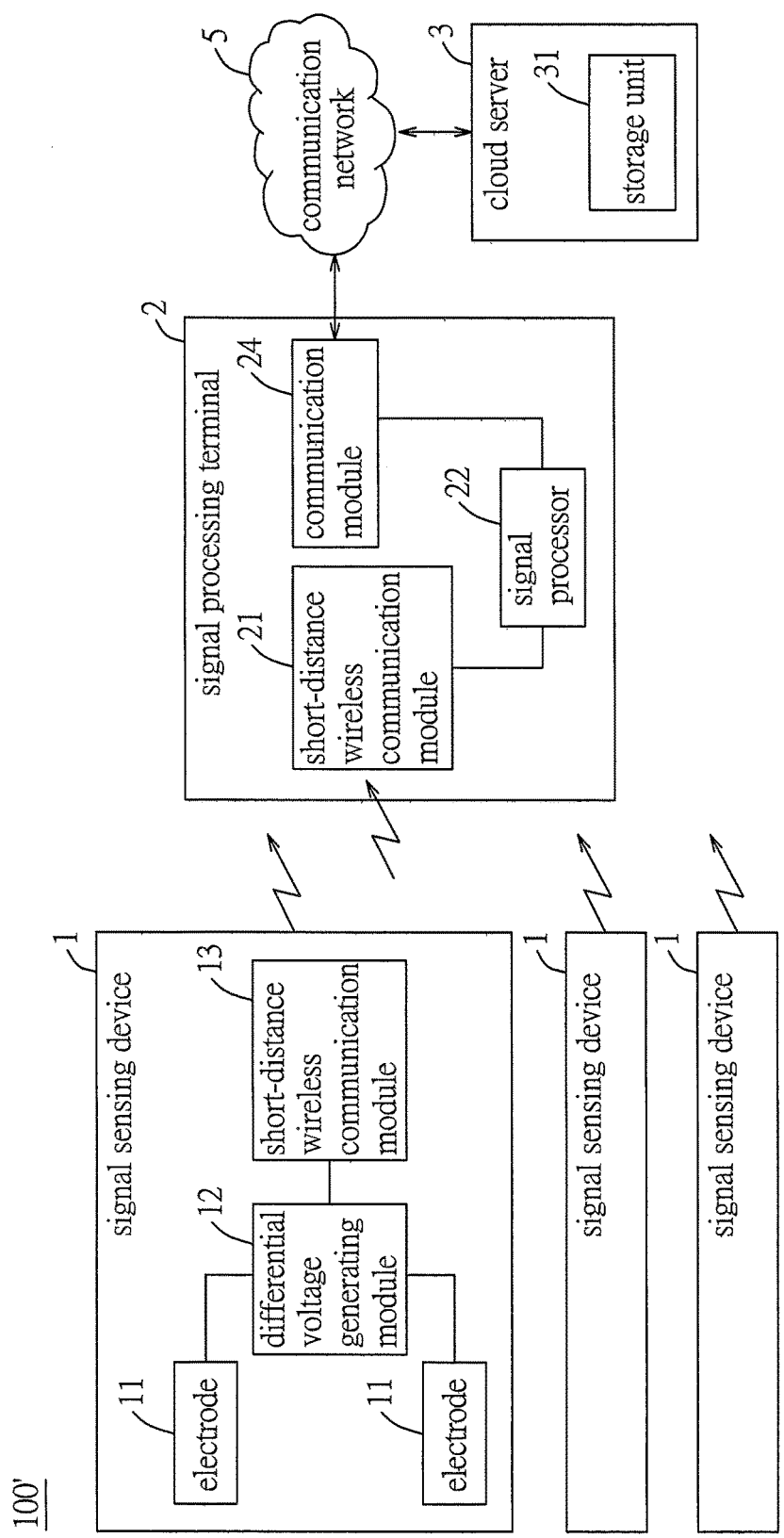
FIG. 6 is a schematic block diagram illustrating the second embodiment of a system for generating twelve-lead ECG signals according to the disclosure.

FIG. 6 illustrates the second embodiment of a system 100' for generating twelve-lead ECG signals according to this disclosure, which is a modification of the first embodiment. Unlike the first embodiment, the system 100' further includes a cloud server 3 connected to a communication network 5, such as the Internet.

In this embodiment, the cloud server 3 includes a storage unit 31. In addition, the signal processing terminal 2 omits the storage unit 23 of the first embodiment shown in FIG. 2, and further includes a communication module 24 connected to the communication network 5. Thus, in use, the (synthesized) twelve-lead ECG signals generated by the signal processor 22 and associated with the user's body are transmitted to the cloud server 3 through the communication module 24 and the communication network 5 such that the cloud server 3 enables the storage unit 31 to store the (synthesized) twelve-lead ECG signals associated with the user's body. In this case, the cloud server 3 can collect and record ECG data associated with the user's body so as to further evaluate cardiac function of the user's body, thereby achieving remote monitoring of the cardiac function of the user's body.

It is noted that, in other embodiments, the system 100' of this disclosure may include a plurality of sets of the three signal sensing devices 1, and a plurality of the signal processing terminals 2 corresponding respectively to the sets of the three signal sensing devices 1. In other words, the system 100' of this disclosure can support ECG measurement and monitoring for many users or patients with heart disease. In this case, the cloud server 3 can be set in medical institutes or related health management agencies so as to simultaneously monitor heart conditions of the multiple users or patients with heart disease.

Figure 7:
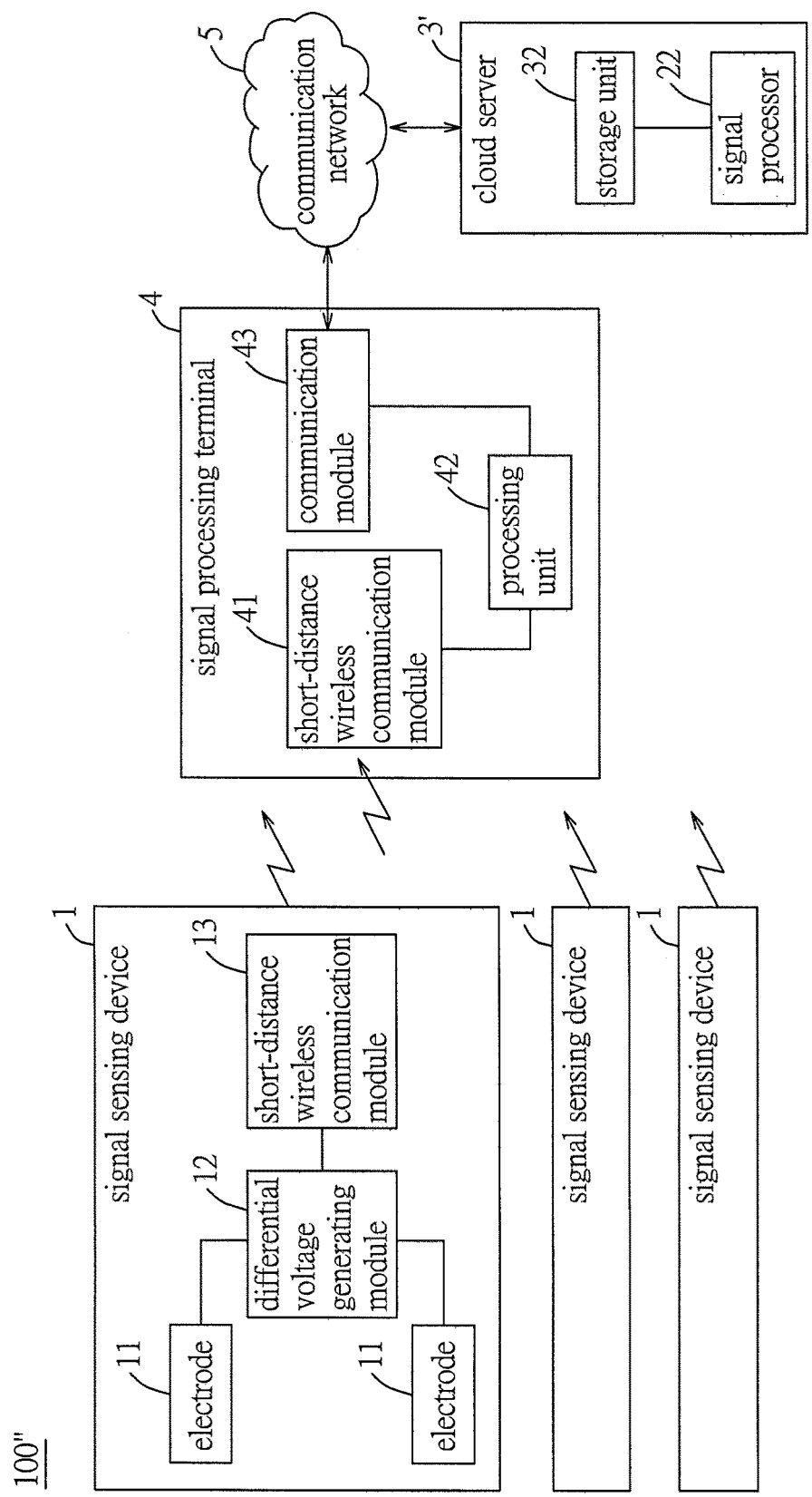
FIG. 7 is a schematic block diagram illustrating the third embodiment of a system for generating twelve-lead ECG signals according to the disclosure.

FIG. 7 illustrates the third embodiment of a system 100" for generating twelve-lead ECG signals according to this disclosure, which is a modification of the first embodiment.

In this embodiment, the signal processing terminal is implemented as a cloud server 3' that is connected to a communication network 5, such as the Internet, and that includes the signal processor 22, and a storage unit 32 coupled to the signal processor 22.

In addition, the system 100" further includes a mobile device 4, for example, a smart phone, a tablet computer or a wearable electronic device having wireless communication capability. The mobile device 4 includes a short-distance wireless communication module 41 similar to the short-distance wireless communication modules 13, 21 of FIG. 2, a communication module 43 connected to the communication network 5, and a processing unit 42 coupled to the short-distance wireless communication module 41 and the communication module 43. It is noted that the mobile device 4 should be carried on the user's body or be disposed within a predetermined communication range of the signal sensing devices 1 attached to the user's body.

In use, the mobile device 4 receives the differential voltages from the signal sensing devices 1 through the short-distance wireless communication module 41. The processing unit 42 transmits, through execution of, for example, an application pre-installed in the mobile device 4, the differential voltages to the cloud server 3' (i.e., the signal processing terminal) via the communication module 43 and the communication network 5. Thereafter, the signal processor 22 of the cloud server 3' generates the (synthesized) twelve-lead ECG signals based on the differential voltages from the mobile device 4 using the dynamic system model, and then enables the storage unit 32 to store the (synthesized) twelve-lead ECG signals thus generated. In this case, similar to the cloud server 3 of FIG. 6, the cloud server 3' can collect and record ECG data associated with the user's body so as to further evaluate cardiac function of the user's body, thereby achieving remote monitoring of the cardiac function of the user's body.

Similar to the system 100' of the second embodiment, the system 100" can also support ECG measurement and monitoring for many users or patients with heart disease. It is noted that, unlike the second embodiment of FIG. 6, only one signal processor 22 included in the cloud server 3' is used to generate and process the twelve-lead ECG signals associated with the multiple users or patients with heart disease.

To sum up, for each user or patient to be monitored, the system 100, 100', 100" of this disclosure utilizes the three signal sensing devices 1, which are sized to facilitate attachment to the user's body respectively at specific locations, to acquire three differential voltages, and then generates, based on the differential voltages, the (synthesized) twelve-lead ECG signals using the dynamic system model, which is pre-established for the user/patient through the aforesaid training procedure of this disclosure.

In addition, since each signal sensing device 1 may be designed to have a compact size of about 10 cm to 15 cm in length, it may be easily attached to the chest of the user's body so that the electrodes 11 thereof are located at the specific locations less susceptible to fat accumulation, thereby effectively reducing noise interference caused by fat. Therefore, the twelve-lead ECG signals generated by the system 100, 100', 100" have relatively high accuracy. Accordingly, the electrocardiogram generated based on the twelve-lead ECG signals has high resemblance to a typical twelve-lead electrocardiogram generated in the conventional manner using ten electrodes.

Moreover, the differential voltages from the signal sensing devices 1 are transmitted to the signal processor 22 using wireless communication. In such a configuration, it is possible to attach the signal sensing devices 1 to the user's body for a long time. Therefore, the system 100, 100', 100" is suitable for long-term ECG measurement and monitoring of the user's body without restriction to mobility of the user.

On the other hand, in some embodiments, due to the presence of the cloud server 3, 3', the system 100', 100" of the disclosure can simultaneously support ECG measurement and monitoring for many users or patients with heart disease.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

The invention claimed is:

1. A method of generating twelve-lead electrocardiogram (ECG) signals to be implemented by a signal processor, said method comprising the steps of:
   i) receiving a plurality of training myoelectric signals, which are sensed respectively by a plurality of test electrodes disposed on the chest of the user's body respectively at separate points during a training period, and twelve standard lead signals measured from the user's body during the training period;
   ii) generating, based on the training myoelectric signals, a plurality of training differential voltages that correspond respectively to a plurality of training differential electrode pairs, each of which consists of a respective adjacent pair of the test electrodes that are disposed at respective distinct locations on the chest of the user's body, each of the training differential voltages being defined as a potential difference between two of the training myoelectric signals sensed by two corresponding adjacent ones of the test electrodes;
   iii) generating, based on the training differential voltages, a plurality of different training differential voltage subsets, each containing three corresponding ones of the training differential voltages;

iv) for each of the training differential voltage subsets, establishing, based on the three corresponding ones of the training differential voltages and on the twelve standard lead signals, a training dynamic system model that is associated with the three corresponding ones of the training differential electrode pairs and that is configured with temporal and spatial correlations among twelve leads of the ECG, and generating, based on the three corresponding ones of the training differential voltages and the training dynamic system model, a corresponding set of twelve synthesized lead signals, which contain eight independent synthesized lead signals corresponding respectively to eight independent leads of the ECG, and four non-independent synthesized lead signals corresponding respectively to four non-independent leads of the ECG; and v) comparing the corresponding set of the twelve synthesized lead signals of each of the training differential voltage subsets respectively with the twelve standard lead signals so as to obtain comparison results corresponding respectively to the training differential voltage subsets;

vi) determining, based on the comparison results and the locations of the test electrodes constituting the training differential electrode pairs, one of the training dynamic system models established in step iv) as a pre-established dynamic system model, and determining the locations at which the test electrodes constituting the three corresponding ones of the training differential electrode pairs associated with said one of the training dynamic system models are disposed as predetermined specific locations of electrodes constituting differential electrode pairs;

vii) receiving three differential voltages, each of which is defined as a potential difference between two corresponding myoelectric signals sensed respectively by two corresponding electrodes that cooperatively constitute a corresponding differential electrode pair that are disposed on a chest of a user's body at the predetermined specific locations; and viii) generating, based on the differential voltages, twelve-lead ECG signals, which include twelve synthesized lead signals, using the pre-established dynamic system model that is associated with the specific locations of the electrodes constituting the differential electrode pairs on the chest of the user's body and that is configured with temporal and spatial correlations among the twelve leads of the ECG, which include the eight independent leads and the four non-independent leads.

2. The method as claimed in claim 1, wherein, in step i), the number of the test electrodes is twenty-four, and the test electrodes are two-dimensionally arranged in a manner that a distance between any two adjacent ones of the test electrodes ranges from 10 cm to 15 cm.

3. The method as claimed in claim 1, wherein, in step iv), for each of the training differential voltage subsets, the training dynamic system model is defined by the following expressions $$x[n]=\tilde{H}\tilde{s}[n]+w[n]$$

$$\tilde{s}[n]=[s[n]^T, s[n-1]^T, \ldots, s[n-L+1]^T]^T$$

$$\tilde{H}=[H_{3\times 8} \, 0_{3\times 8(L-1)}],$$

where $x[n]$ is a $3\times 1$ vector and represents the three corresponding ones of the training differential voltages at time n, $\tilde{s}[n]$ is an $8L\times 1$ vector and represents signals at time n that correspond respectively to the eight independent leads, that characterize the temporal and spatial correlations among the eight independent leads of the twelve leads and that conform to an $L^{th}$-order autoregression (AR(L)) model, L is a predetermined order number, $\tilde{H}$ is a $3\times 8L$ matrix and is associated with a transformation matrix $H_{3\times 8}$ obtained from the three corresponding ones of the training differential voltages and the twelve standard lead signals, and $w[n]$ is a $3\times 1$ noise vector at time n and is obtained from the three corresponding ones of the training differential voltages and the twelve standard lead signals.

4. The method as claimed in claim 3, wherein $\tilde{s}[n]$ is dynamically represented, using the AR(L) model, by $$\tilde{s}[n]=F\tilde{s}[n-1]+Bv[n],$$

where F is an $8L\times 8L$ matrix and characterizes the temporal and spatial correlations among the eight independent leads of the twelve leads, B is an $8L\times 8$ noise power matrix, and $v[n]$ is an $8\times 1$ noise vector at time n.

5. The method as claimed in claim 4, wherein, in step iv), for each of the individual training differential voltage subsets, the corresponding set of the twelve synthesized lead signals is generated based on $x[n]$, $\tilde{s}[n]$ and $\tilde{H}$ using filtering processing.

6. The method as claimed in claim 5, wherein, in step iv), for each of the individual training differential voltage subsets, eight independent synthesized lead signals $\hat{s}[n]$ of the corresponding set of the twelve synthesized lead signals is represented by $$\hat{s}[n]=F\hat{s}[n-1]+K[n](x[n]-\tilde{H}\hat{s}[n-1]),$$

where $K[n]$ is an $8L\times 3$ filter gain matrix at time n, and four non-independent synthesized lead signals of the corresponding set of the twelve synthesized lead signals are generated based on $\hat{s}[n]$.

7. The method as claimed in claim 1, wherein, in step vi):
correlation coefficients between the corresponding set of the twelve synthesized lead signals associated with said one of the training dynamic system models and the twelve standard lead signals are relatively large; and
the specific locations of the electrodes constituting the differential electrode pairs are around the heart of the user's body.

8. The method as claimed in claim 7, wherein the specific locations of the electrodes constituting a first one of the differential electrode pairs are between the upper right side edge of the heart of the user's body and a collarbone of the user's body, the specific locations of the electrodes constituting a second one of the differential electrode pairs are on the lower left side edge of the heart of the user's body, and the specific locations of the electrodes constituting a third one of the differential electrode pairs are on the right side of the heart of the user's body.

9. A system for generating twelve-lead electrocardiogram (ECG) signals, comprising:
a signal processing terminal configured to
receive a plurality of training myoelectric signals, which are sensed respectively by a plurality of test electrodes disposed on the chest of the user's body respectively at separate points during a training period, and twelve standard lead signals measured from the user's body during the training period,
generate, based on the training myoelectric signals, a plurality of training differential voltages that correspond respectively to a plurality of training differential electrode pairs, each of which consists of a respective adjacent pair of the test electrodes that are disposed at respective distinct locations on the chest of the user's body, each of the training differential voltages being defined as a potential difference between two of the training myoelectric signals sensed by two corresponding adjacent ones of the test electrodes, generate, based on the training differential voltages, a plurality of different training differential voltage subsets, each containing three corresponding ones of the training differential voltages, for each of the training differential voltage subsets, establish, based on the three corresponding ones of the training differential voltages and on twelve standard lead signals, a training dynamic system model that is associated with the three corresponding ones of the training differential electrode pairs and that is configured with temporal and spatial correlations among twelve leads of an ECG, and generating, based on the three corresponding ones of the training differential voltages and the training dynamic system model, a corresponding set of twelve synthesized lead signals, which contain eight independent synthesized lead signals corresponding respectively to eight independent leads of the ECG, and four non-independent synthesized lead signals corresponding respectively to four non-independent leads of the ECG, compare the corresponding set of the twelve synthesized lead signals of each of the training differential voltage subsets respectively with the twelve standard lead signals so as to obtain comparison results corresponding respectively to the training differential voltage subsets, and determine, based on the comparison results and the locations of the test electrodes constituting the training differential electrode pairs, one of the training dynamic system models established in step iv) as a pre-established dynamic system model, and determine the locations at which the test electrodes constituting the three corresponding ones of the training differential electrode pairs associated with said one of the training dynamic system models are disposed as predetermined specific locations of electrodes constituting the differential electrode pairs; and three signal sensing devices attachable to a chest of a user's body, each of said signal sensing devices including two spaced apart electrodes that cooperatively constitute a corresponding differential electrode pair and that are to be disposed on the chest of the user's body at the predetermined specific locations, and being configured to sense two myoelectric signals through said electrodes thereof so as to generate a corresponding differential voltage that is defined as a potential difference between the myoelectric signals, wherein the signal processing terminal is further configured to receive the differential voltages respectively therefrom in a wireless manner, said signal processing terminal being operable to generate, based on the differential voltages, the twelve-lead ECG signals, which include twelve synthesized lead signals, using the pre-established dynamic system model that is associated with the specific locations of said electrodes of said signal sensing devices on the chest of the user's body and that is configured with temporal and spatial correlations among the twelve leads of the ECG, which include the eight independent leads and the four non-independent leads.

10. The system as claimed in claim 9, wherein, for each of said signal sensing devices, a distance between said electrodes ranges from 10 cm to 15 cm.

11. The system as claimed in claim 9, wherein the dynamic system model is defined by the following expressions $$x[n]=\tilde{H}\tilde{s}[n]+w[n]$$

$$\tilde{s}[n]=[s[n]^T,s[n-1]^T,\ldots,s[n-L+1]^T]^T$$

$$\tilde{H}=[H_{3\times 8}\,0_{3\times 8(L-1)}],$$

where $x[n]$ is a 3×1 vector and represents the three training differential voltages at time n, $\tilde{s}[n]$ is an 8L×1 vector and represents signals at time n that correspond respectively to the eight independent leads, that characterize the temporal and spatial correlations among the eight independent leads and that conforms to an $L^{th}$-order autoregression (AR(L)) model, L is a predetermined order number, $\tilde{H}$ is a 3×8L matrix and is associated with a transformation matrix $H_{3\times 8}$ obtained from the training data, and w [n] is a 3×1 noise vector at time n and is obtained from the training data.

12. The system as claimed in claim 11, wherein $\tilde{s}[n]$ is dynamically represented, using the AR(L) model, by $$\tilde{s}[n]=F\tilde{s}[n-1]+Bv[n],$$

where F is an 8L×8L matrix and characterizes the temporal and spatial correlations among the eight independent leads of the twelve leads, B is an 8L×8 noise power matrix, and v [n] is an 8×1 noise vector at time n.

13. The system as claimed in claim 12, wherein the twelve synthesized lead signals are generated based on $x[n]$, $\tilde{s}[n]$ and $\tilde{H}$ using filtering processing.

14. The system as claimed in claim 13, wherein eight $\hat{s}[n]$ of the twelve synthesized lead signals corresponding respectively to the eight independent leads are represented by $$\hat{s}[n]=F\hat{s}[n-1]+K[n](x[n]-\tilde{H}F\hat{s}[n-1])$$

where $K[n]$ is an 8L×3 filter gain matrix at time n, and the remaining four of the twelve synthesized lead signals corresponding respectively to the four non-independent leads are generated based on $\hat{s}[n]$.

15. The system as claimed in claim 9, wherein the specific locations of said electrodes of said signal sensing devices on the chest of the user's body are disposed around a heart of the user's body.

16. The system as claimed in claim 15, wherein the specific locations of said electrodes of a first one of said signal sensing devices are at a position between the upper right side edge of the heart of the user's body and a collarbone of the user's body, the specific locations of said electrodes of a second one of said signal sensing devices are on the lower left side edge of the heart of the user's body and the specific locations of said electrodes of a third one of said signal sensing devices are on the right side of the heart of the user's body.

17. The system as claimed in claim 9, wherein said signal processing terminal is a mobile device that is carried on the user's body and that receives the differential voltages from said signal sensing devices via short distance wireless communication.

18. The system as claimed in claim 17, further comprising a cloud server that communicates with said mobile device through a communication network;

wherein said mobile device transmits the twelve-lead ECG signals generated thereby to said cloud server via said communication network such that said cloud server collects and records the twelve-lead ECG signals so as to evaluate cardiac function of the user's body.

19. The system as claimed in claim 9, further comprising a mobile device that receives the differential voltages from said signal sensing devices via short distance wireless communication and that is connected to said signal processing terminal through a communication network for transmitting the differential voltages thereto;

wherein said signal processing terminal is a cloud server that further stores the twelve-lead ECG signals generated thereby so as to evaluate cardiac function of the user's body.

* * * * *